(12) United States Patent
Jo et al.

(10) Patent No.: US 10,525,165 B2
(45) Date of Patent: Jan. 7, 2020

(54) DENTAL BARRIER MEMBRANE USING COCOON AND METHOD FOR MANUFACTURING SAME

(71) Applicant: REPUBLIC OF KOREA (MANAGEMENT:RURAL DEVELOPMENT ADMINISTRATION), Jeonju-si, Jeollabuk-do (KR)

(72) Inventors: You Young Jo, Jeollabuk-do (KR); Hae Yong Kweon, Suwon-si (KR); Kwang Gill Lee, Suwon-si (KR); Joo Hong Yeo, Suwon-si (KR); Heui Sam Lee, Suwon-si (KR)

(73) Assignee: Republic of Korea (Management: Rural Development Administration), Jeonju-si, Jeollabuk-do (KR)

( * ) Notice: Subject to any disclaimer, the term of this patent is extended or adjusted under 35 U.S.C. 154(b) by 280 days.

(21) Appl. No.: 15/326,747

(22) PCT Filed: Jul. 28, 2015

(86) PCT No.: PCT/KR2015/007848
§ 371 (c)(1),
(2) Date: Jan. 17, 2017

(87) PCT Pub. No.: WO2016/021859
PCT Pub. Date: Feb. 11, 2016

(65) Prior Publication Data
US 2017/0203003 A1    Jul. 20, 2017

(30) Foreign Application Priority Data

Aug. 4, 2014  (KR) .................. 10-2014-0099678

(51) Int. Cl.
*A61K 35/64*   (2015.01)
*A61L 27/36*   (2006.01)
*A61L 31/00*   (2006.01)
*A61C 8/02*    (2006.01)
*A61K 35/63*   (2015.01)
*A61L 27/54*   (2006.01)

(52) U.S. Cl.
CPC ........ *A61L 27/3604* (2013.01); *A61C 8/0006* (2013.01); *A61K 35/63* (2015.01); *A61K 35/64* (2013.01); *A61L 27/365* (2013.01); *A61L 27/3691* (2013.01); *A61L 27/54* (2013.01); *A61L 31/005* (2013.01); *A61L 2300/412* (2013.01); *A61L 2430/12* (2013.01)

(58) Field of Classification Search
None
See application file for complete search history.

(56) References Cited

U.S. PATENT DOCUMENTS

| | | |
|---|---|---|
| 2004/0005363 A1 | 1/2004 | Tsukada et al. |
| 2004/0097709 A1 | 5/2004 | Armato et al. |
| 2006/0095137 A1 | 5/2006 | Chung et al. |
| 2009/0214649 A1* | 8/2009 | Gazit .................... A61L 27/225 424/484 |
| 2010/0286774 A1 | 11/2010 | Kweon et al. |

FOREIGN PATENT DOCUMENTS

| | | | |
|---|---|---|---|
| JP | 06-166850 | * | 6/1994 |
| JP | 06-166850 A | | 6/1994 |
| KR | 10-2003-0097691 A | | 12/2003 |
| KR | 10-2006-0038096 A | | 5/2006 |
| KR | 10-2010-0121169 A | | 11/2010 |
| KR | 10-2014-0003942 A | | 1/2014 |
| KR | 10-1403473 B1 | | 6/2014 |

OTHER PUBLICATIONS

Chen (Acta Biomaterialia (2012), vol. 8, pp. 2620-2627).*
Zhao (Polymer (20050, vol. 46, pp. 9192-9201).*
Ha (Macromolecular Research (2014), vol. 22, No. 9, pp. 1018-1023).*
Seok (J Craniofac Surg (2014), vol. 25, pp. 2066-2069).*
You-Young Jo et al., "Preparation and characterization of medical silk sponge", J. Seric Entomol Sc., 2013, pp. 68-72, vol. 51, No. 1.
Korean Office Action dated May 1, 2015.

* cited by examiner

*Primary Examiner* — Susan Hoffman
(74) *Attorney, Agent, or Firm* — Rabin & Berdo, P.C.

(57) ABSTRACT

Disclosed herein are a cocoon-based, dental barrier membrane for guided bone regeneration and a method for manufacturing the same. The cocoon-based, dental barrier membrane is manufactured by dividing a cocoon into two or more fragments in a predetermined form, the cocoon having a shell having a first thickness. The dental barrier membrane is biocompatible, has excellent tensile strength and porosity, and promotes osteogenesis in a bone defect.

8 Claims, 8 Drawing Sheets

DENTAL BARRIER MEMBRANE USING COCOON AND METHOD FOR MANUFACTURING SAME

TECHNICAL FIELD

The present invention relates to a dental barrier membrane for guided bone regeneration using a cocoon, and a manufacturing method thereof. More particularly, the present invention relates to a cocoon-based barrier membrane that is biocompatible, has excellent tensile strength, and promotes osteogenesis in bone defects, and a method for manufacturing the same.

BACKGROUND ART

A dental barrier membrane for guided bone regeneration is a device used in dental surgery, such as implants, to induce bone regeneration in a bone defect. When applied to a bone defect, a dental barrier membrane functions to mechanically block the migration of epithelial or connective tissue cells into the bone defect, thus retaining the space until bone regeneration.

At first, dental barrier membranes were made of non-biodegradable materials such as polytetrafluoroethylene, cellulose acetate, silicon rubber, or polyurethane. However, barrier membranes made of non-biodegradable synthetic polymers are apt to cause inflammation or tissue necrosis because of their poor biocompatibility.

To overcome such problems, biocompatible, natural materials for use in biodegradable barrier membranes have recently been studied. There are no significant differences in bone regeneration between biodegradable barrier membranes and non-biodegradable barrier membranes. When applied in clinical practice, however, the biodegradable barrier membranes developed thus far cannot retain their shapes due to their insufficient tensile strength, and thus are likely to fail in securing the space where the tissue of interest is to grow, which may lead to secondary inflammation.

Now, research has been directed toward the development of materials for dental barrier membranes that are biocompatible and have sufficient tensile strength to allow the barrier membranes to retain their shape.

With regard to the related art, reference may be made to Korean Patent Unexamined Publication Application No. 10-2014-0003942 (issued on Jan. 10, 2014, titled "Dental Barrier Membrane Having Good Growth of Soft Tissues or Bone Tissues") and Korean Patent No. 10-1403473 (issued on Jun. 11, 2014, titled "Dental Membrane").

DISCLOSURE

Technical Problem

It is an object of the present invention to provide a biocompatible, cocoon-based dental barrier membrane that has excellent tensile strength and porosity and which promotes osteogenesis in bone defects, and a method for manufacturing the same.

It is another object of the present invention to provide a cocoon-based dental barrier membrane that can be relatively simply manufactured in a more cost-efficient manner than conventional artificial barrier membranes, and a method for manufacturing the same.

Embodiments of the present invention will be described in detail with reference to the accompanying drawings. These embodiments will be described in detail in order to allow those skilled in the art to practice the present invention. It should be appreciated that various embodiments of the present invention are different, but are not necessarily exclusive. For example, specific shapes, configurations, and characteristics described in an embodiment of the present invention may be implemented in another embodiment without departing from the spirit and the scope of the present invention. In addition, it should be understood that the positions and arrangements of individual components in each disclosed embodiment may be changed without departing from the spirit and the scope of the present invention. Therefore, the detailed description provided below should not be construed as being restrictive. In addition, the scope of the present invention is defined only by the accompanying claims and their equivalents if appropriate.

Technical Solution

In order to accomplish the above objects, an aspect of the present invention provides a cocoon-based dental barrier membrane, which is prepared by dividing a cocoon having a first shell thickness into two or more fragments having a predetermined form.

In one exemplary embodiment of the present invention, each of the fragments is delaminated into a lamellar fragment having a second thickness, the second thickness being smaller than the first thickness.

In another exemplary embodiment of the present invention, the lamellar fragment having a second thickness is an inner, middle, or outer stratum of the cocoon.

In another exemplary embodiment of the present invention, the lamellar fragment is sterilized or packed.

In accordance with another aspect thereof, the present invention provides a method for manufacturing a cocoon-based dental barrier membrane, comprising a first step of dividing a cocoon into two or more fragments having a predetermined form, the cocoon having a shell having a first thickness.

In one exemplary embodiment of the present invention, the method may further comprise a second step of delaminating each of the fragments into a lamellar fragment having a second thickness, the second thickness being smaller than the first thickness.

In another exemplary embodiment of the present invention, the method may further comprise a third step of packing the fragments of the second thickness prepared in the second step.

In another exemplary embodiment of the present invention, the method may further comprise conducting sterilization before or after each step.

In another exemplary embodiment of the present invention, the lamellar fragment having a second thickness is an inner, middle or outer stratum of the cocoon.

Advantageous Effects

The cocoon-based dental barrier membrane of the present invention can be prepared easily, and thus in a cost-efficient manner, compared to conventional dental barrier membranes.

In addition to be biocompatible, the dental barrier membrane of the present invention has high tensile strength and porosity, and can promote osteogenesis in bone defects.

BEST MODE

Unless otherwise defined, all terms used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

The term "dental barrier membrane," as used herein, refers to a barrier membrane designed to reconstruct bone tissues that have defects due to various dental diseases. The dental barrier membrane should significantly improve osteogenesis in bone defects or around implants, be hard enough to be sutured, and have biocompatibility for safe use in vivo.

In addition, a dental barrier membrane for guided bone regeneration is required to avoid post-operative infection and tissue degeneration, and closely adhere to periodontal tissues without giving a sensation of irritation. Importantly, dental barrier membranes should guarantee cell growth.

When hydrolyzed in vivo, however, most conventional dental barrier membranes cause the generation of acids such as lactic acid, glycolic acids, etc, which lower the pH in a local region, causing inflammation and histotoxicity. Further, for obtaining the desired properties, the dental barrier membranes used to date require pretreatment processes, such as physical crosslinking, etc. However, such pretreated dental barrier membranes may be toxic to the body and remain as foreign matter upon long-term use in vivo.

Leading to the present invention, intensive and thorough research into a dental barrier membrane for guided bone regeneration, conducted by the present inventor, resulted in the finding that a fragment prepared from a cocoon is biocompatible and useful as a biomembrane not only because it has high tensile strength and porosity but also because it can promote osteogenesis in a bone defect, and that the fragment can be produced at significantly lower cost, compared to conventional dental barrier membranes.

Figure 1:
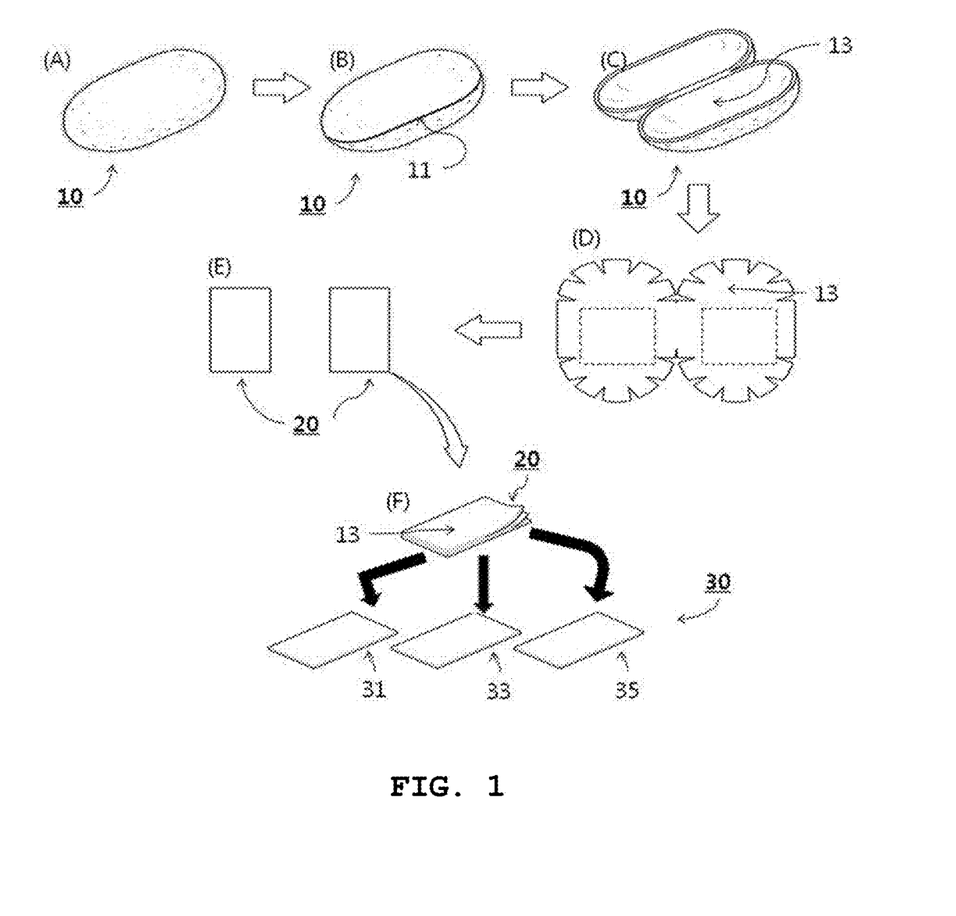
FIG. 1 is a schematic view illustrating a procedure of manufacturing a cocoon-based, dental barrier membrane for guided bone regeneration according to one embodiment of the present invention.

With reference to FIG. 1, the method for manufacturing a cocoon-based dental barrier membrane for guided bone regeneration in accordance with the present invention is explained below.

1. Step 1: Preparation of Cocoon Fragment having First Thickness.

As shown in FIG. 1A, a cocoon 10, the shell of which has a first thickness, is prepared.

A cocoon is a casting spun of silk by silkworms and is used as a material for silk fibers. In the present invention, cocoons, which may be unused resources, are up-cycled into a new high value-added product, thus bringing economic benefits to silkworm farmers. Naturally constructed by silkworms, which eat clean mulberry leaves, cocoons are free of toxicity and are suitable for use as an environment-friendly material.

Hence, the present invention takes a cocoon 10 as a material for a dental barrier membrane. The cocoon 10 is processed, as shown in FIGS. 1B to 1E, into two or more planar fragments, each having a first thickness.

In greater detail, the oval cocoon 10 is dissected along a cutting line 11 into halves, as shown in FIG. 1B. The dissected halves have semi-oval shapes, and are opened to expose the inside surface 13 of the cocoon, as shown in FIG. 1C.

Next, the cocoon halves with curved inside surfaces 13 are planarized to some degree by cutting many sites along the edge as shown in FIG. 1D, and planar regions are cut out to obtain cocoon fragments having a first thickness, as shown in FIG. 1E.

The dental barrier membrane prepared in the present invention need not have a planar surface. Because a cocoon originally has an elliptical ball shape, the curved shape of the dissected cocoon may be utilized to yield curved dental barrier membranes if necessary. For use as a small dental barrier membrane for guided bone regeneration, a cocoon fragment having a small area may be relatively planar. In contrast, when a relatively large area of the dissected cocoon halves is taken, the dental barrier membranes may have curved surfaces.

Figure 2:
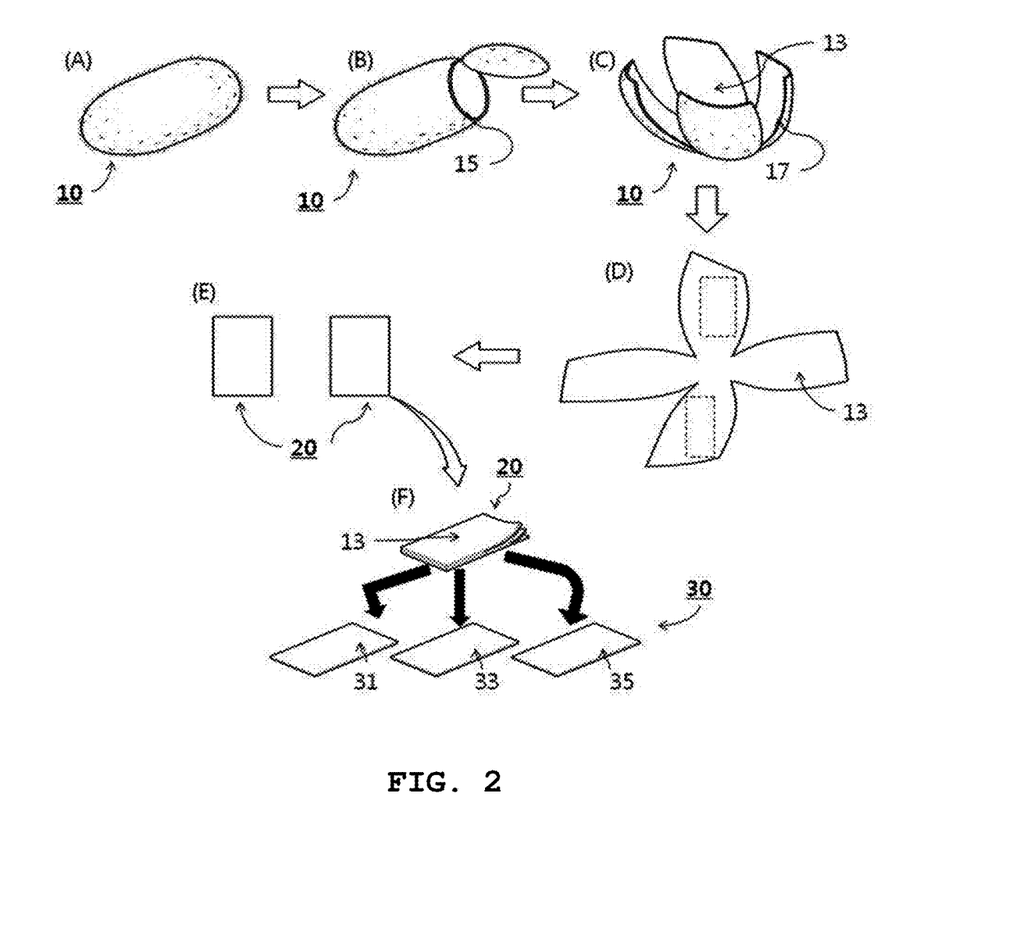
FIG. 2 is a schematic view illustrating the procedure of manufacturing a cocoon-based, dental barrier membrane for guided bone regeneration according to a modified embodiment of the present invention.

With reference to FIG. 2, a modified method for preparing a cocoon fragment having a first thickness is described. In detail, an oval-shaped cocoon 10 is cut along a second cutting line 15 and a third cutting line 17 to expose the inside 13 of the cocoon 10, as shown in FIGS. 2B and 2C. Then, the dissected cocoon having a curved surface is spread as shown in FIG. 2D, and then cocoon fragments 20 having a first thickness are obtained as shown in FIG. 2E.

The preparation methods of cocoon fragments described in FIGS. 1 and 2 are only illustrative, but are not given as limitative embodiments. A cocoon fragment having a first thickness may be prepared by cutting a cocoon in the manners shown in FIGS. 1 and 2, but other cutting methods may be used.

2. Step 2: Preparation of Cocoon Fragment having Second Thickness (Dental Barrier Membrane)

Because the cocoon fragments 20 having a first thickness, prepared in step 1, have a multilayer structure identical to that of the cocoon shell, the multilayer structure may be split into thinner layers for use as a dental barrier membrane.

Although the cocoon fragment 20 having a first thickness, prepared in step 1, is itself usable as a dental barrier membrane, it is subjected to thickness splitting to give cocoon fragments 30 having a second thickness. In this regard, the second thickness is smaller than the first thickness. As mentioned above, the cocoon fragment having the first thickness may be itself used as a dental barrier membrane without splitting to reduce the thickness thereof.

As they are, the cocoon fragments 30 can be applied as dental barrier membranes for any purpose. If necessary, they may be sterilized or chemically treated.

A cocoon shell varies in thickness (first thickness) from 0.3 to 1.0 mm depending on the silkworm species. In principal, any kind of cocoon may be used in the present invention. For the purpose of the present invention, a cocoon having a shell thickness of 0.5~0.8 mm is employed.

A cocoon fragment can be easily delaminated into up to 16 lamellas, although the number of delaminations is dependent on the shell thickness. The thicknesses of the lamellas can be determined according to the strength and elongation necessary for the kind and use of the dental barrier membrane. From a cocoon having a shell thickness of 0.5~0.8 mm, a dental barrier membrane 0.01 mm~0.7 mm thick can be prepared by delamination. According to the use of the dental barrier membrane, selection may be made of cocoon fragments 30 having various thicknesses.

MODE FOR INVENTION

A better understanding of the present invention may be obtained through the following examples that are set forth to illustrate, but are not to be construed as limiting the present invention.

<Example 1> Preparation of Dental Barrier Membrane

Figure 3:
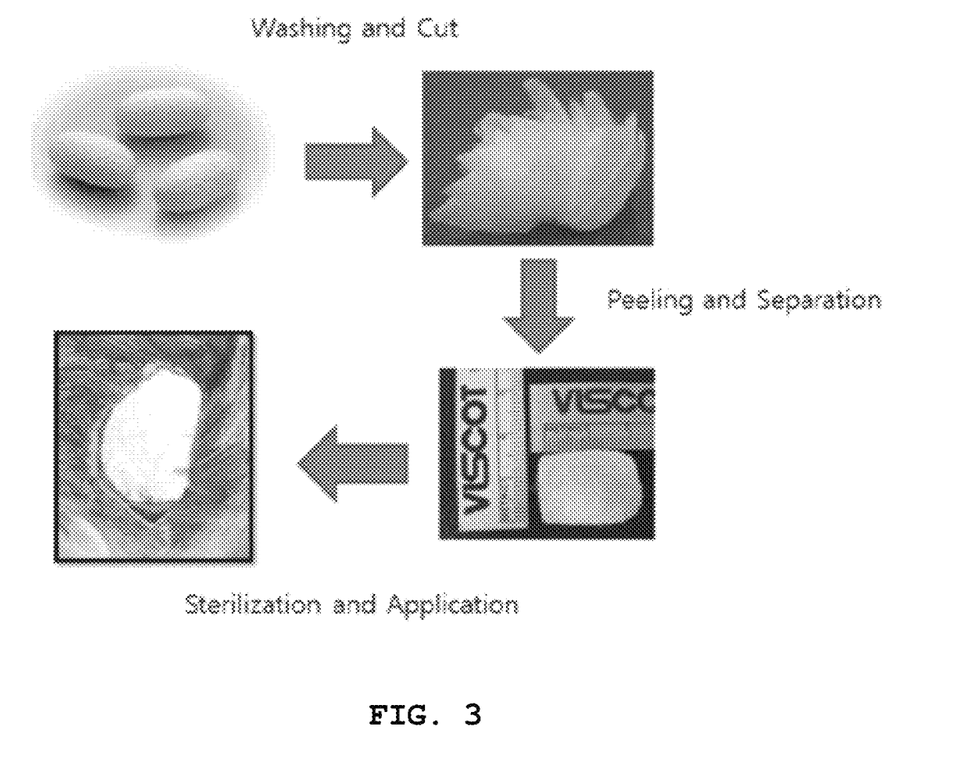
FIG. 3 shows photographs of cocoons and cocoon fragments in a process of manufacturing dental barrier membranes in accordance with the present invention.

The procedure of manufacturing a dental barrier membrane in accordance with the present invention is illustrated in FIG. 3. First, a cocoon 10 was prepared, and cut at a proper site to expose the inside thereof.

Next, the cut cocoon was further processed to make the curved inside planar. The planarized cocoon was cut into rectangular fragments 20.

The cocoon fragments 20 were peeled into strata having a suitable thickness, followed by sterilizing the strata to afford dental barrier membranes.

<Test Example 1> Morphology of Dental Barrier Membranes from Cocoon

1. Test Method

Morphologies of the dental barrier membranes prepared in Examples 1 to 3 were observed by scanning electron microscopy (SEM), with commercially available collagen and PTFE (polytetrafluoroethylene) barrier membranes used as controls for comparison.

2. Test Results

Figure 4:
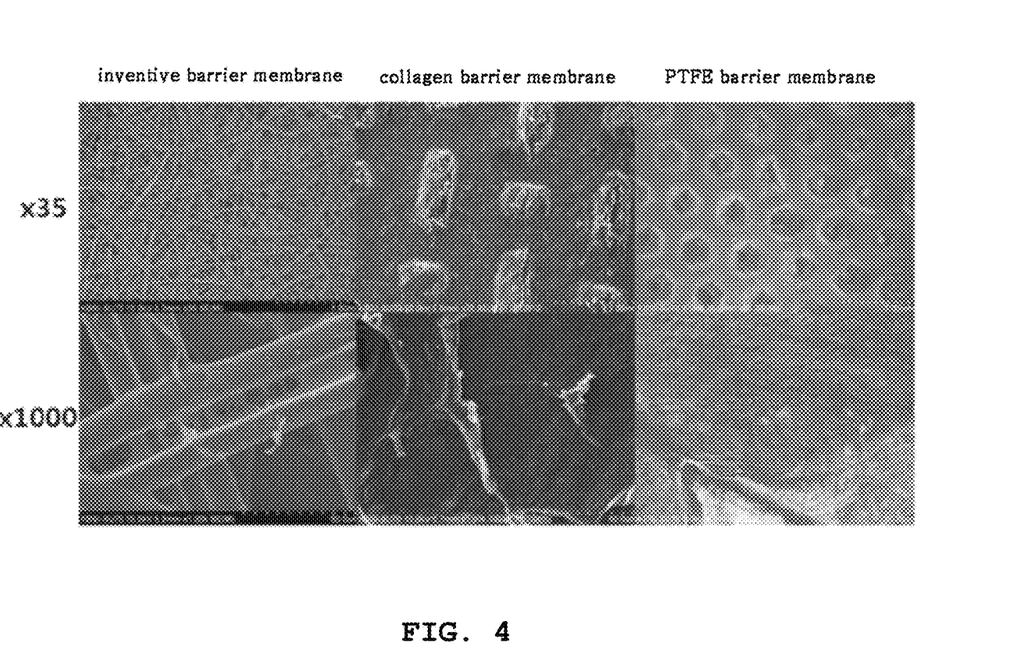
FIG. 4 shows the morphologies of cocoon fragments used in the dental barrier membranes of the present invention.

As can be seen in FIG. 4, there were distinct differences in pore form and surface morphology between the dental barrier membrane of the present invention and the control, as observed by SEM. On the planar surface of the collagen barrier membrane, relatively large pores were arranged in a uniform pattern while the PTFE barrier membrane had regular arrangements of pores having constant sizes on planar surfaces.

In contrast, the dental barrier membrane of the present invention was observed to have many plies of irregularly entangled fibrous strands various in thickness, with many pores among the fibrous strands. Having a porous structure highly transmissive to nutrients and water, the dental barrier membrane of the present invention is therefore expect to find effective applications in osteogenesis at bone defects thanks to its ability to allow for the supply of nutrients and water necessary for bone regeneration.

<Test Example 2> Mechanical Properties of Cocoon-Based Barrier Membrane

1. Test Method

The physical properties of the cocoon-based dental barrier membranes prepared in Example 1 were measured. In this regard, a tensile test was conducted using a universal testing machine (DAEYEONG, Korea), with commercially available barrier membranes made of collagen or PTFE (polytetrafluoroethylene) serving as controls.

Test specimens having sizes of 5×20 (width×length) mm were used. The specimens were extended at a rate of 10 mm/min, with an initial gauge length set to be 10 mm.

In addition, considering the fact that dental barrier membranes, when used in the mouth, are continuously wetted with saliva, the specimens were immersed for 1 hr in physiological saline before the measurement of the mechanical properties (tensile strength).

2. Test Results

TABLE 1

| | Tensile Strength (MPa) | Modulus of Elasticity |
|---|---|---|
| Inventive Barrier Membrane | 27.6 ± 1.5 | 39.5 ± 3.1 |
| Collagen Barrier Membrane | 3.5 ± 1.3 | 9.6 ± 2.2 |
| PTFE Barrier Membrane | 4.3 ± 1.7 | 304.5 ± 5.3 |

The dental barrier membrane of the present invention and the controls, all being wetted, were measured for tensile strength and modulus of elasticity, and the results are given in Table 1. Tensile strength was measured to be 27.6±1.5 MPa in the barrier membrane of the present invention, 3.5±1.3 MPa in the collagen barrier membrane, and 4.3±1.7 MPa in the PTFE membrane. In addition, the modulus of elasticity was measured to be 39.5±3.1 in the barrier membrane of the present invention, 9.6±2.2 MPa in the collagen barrier membrane, and 304.5±5.3 MPa in the PTFE membrane.

As can be seen, the barrier membrane of the present invention exhibited tensile strength 9 times higher than that of the collagen barrier membrane, and 7 times higher than that of the PTFE barrier membrane. Also, the barrier membrane of the present invention is elastic, as the modulus of elasticity was 4 times higher than that of the collagen barrier membrane.

Figure 5:
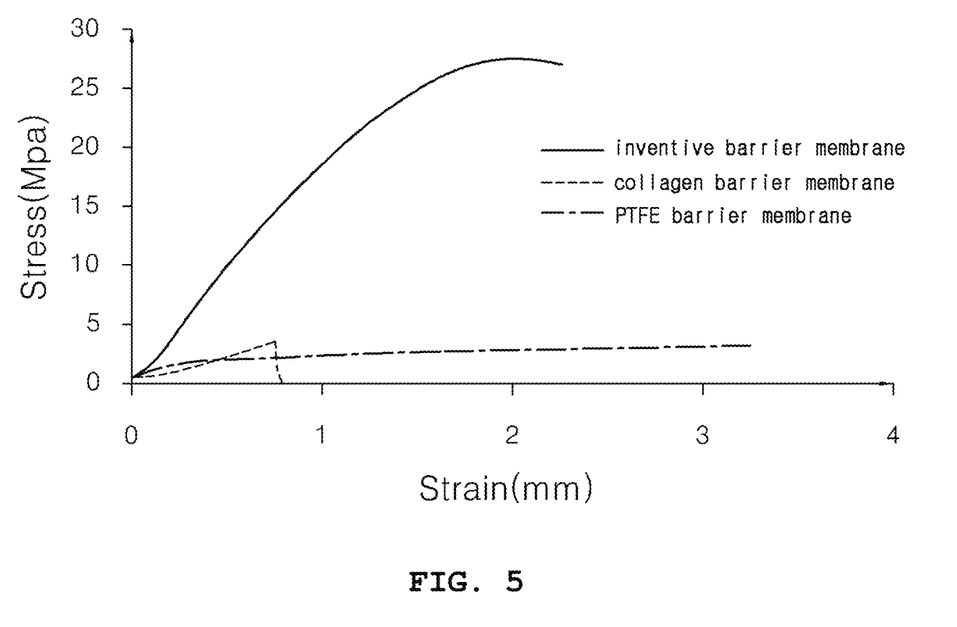
FIG. 5 is a graph showing a mechanical property (the tensile strength) of the cocoon-based dental barrier membrane of the present invention, with conventional barrier membranes used as controls.

Next, FIG. 5 is graph in which stresses are plotted against strains in the barrier membrane of the present invention, the collagen barrier membrane, and the PTFE barrier membrane. The PTFE barrier membrane was observed to greatly increase only in elongation within the range where a relatively large increase in tensile strength occurred. The collagen barrier membrane underwent fracture before a great increase in tensile strength. In contrast, the barrier membrane of the present invention increased in elongation with the increase of tensile strength. Accordingly, the barrier membrane of the present invention has higher tensile strength than do conventional collagen or PTFE barrier membranes.

For use in tissue regeneration and osteogenesis in vivo, the barrier membrane should maintain its shape and have tensile strength, modulus of elasticity, and elongation large enough to withstand pressures in implanted regions. The cocoon-based membrane of the present invention is superior in tensile strength, modulus of elasticity, and elongation to commercially available controls, and thus is suitable for use as a dental barrier membrane.

<Test Example 3> Bone Regeneration Effect of Cocoon-Based Dental Barrier Membrane 1. Test Method The dental barrier membrane prepared in Example 1 was implanted into a bone defect of rabbits, with a collagen barrier membrane or PTFE (polytetrafluoroethylene) barrier membrane serving as a control.

The formation of new bone was examined by μ-CT (micro-computerized tomography), Masson's trichrome staining, and histological analysis at 4 and 8 weeks after the implantation of the barrier membranes.

Figure 6:
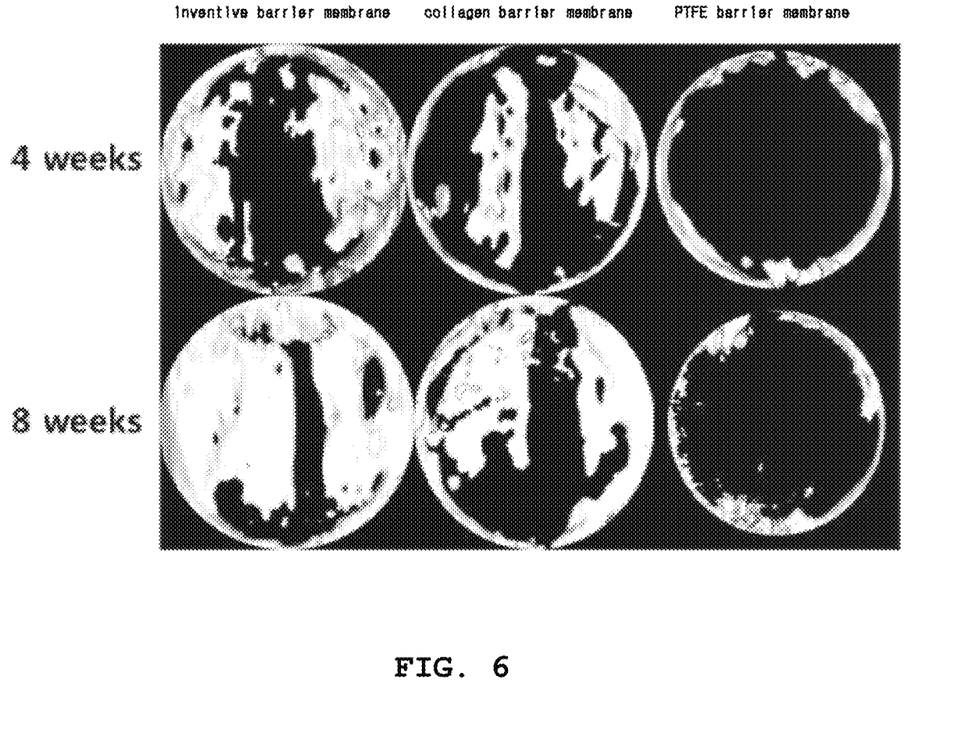
FIG. 6 shows μ-CT (micro-computerized tomography) images of new bone formed in bone defects implanted with the dental barrier membrane of the present invention or control barrier membranes.

2. Test Results

μ-CT (micro-computerized tomography) images of new bone formed after implantation of the dental barrier membrane of the present invention or control barrier membranes are given in FIG. 6. In the images, newly formed bone appears white.

At post-operative week 4, new bone tissue was difficult to detect in the bone defect implanted with the PTFE barrier membrane, and occupied about ⅓ of the bone defect implanted with the collagen barrier membrane. The bone defect implanted with the barrier membrane of the present invention was ⅔ filled with new bone.

Even at post-operative week 8, it was still difficult to detect new bone in the PTFE barrier membrane-implanted bone defect, with little difference from post-operative week 4. The collagen barrier membrane allowed for the formation of new bone over about ⅔ of the overall bone defect, which was improved compared to post-operative week 4.

Over the overall region of the bone defect implanted with the barrier membrane of the present invention was formed new bone tissue, with a significant improvement compared to that at post-operative week 4. Thus, the barrier membrane of the present invention notably exhibited much more efficient bone regeneration effects over the same period of time than did conventional barrier membranes.

Figure 7A:
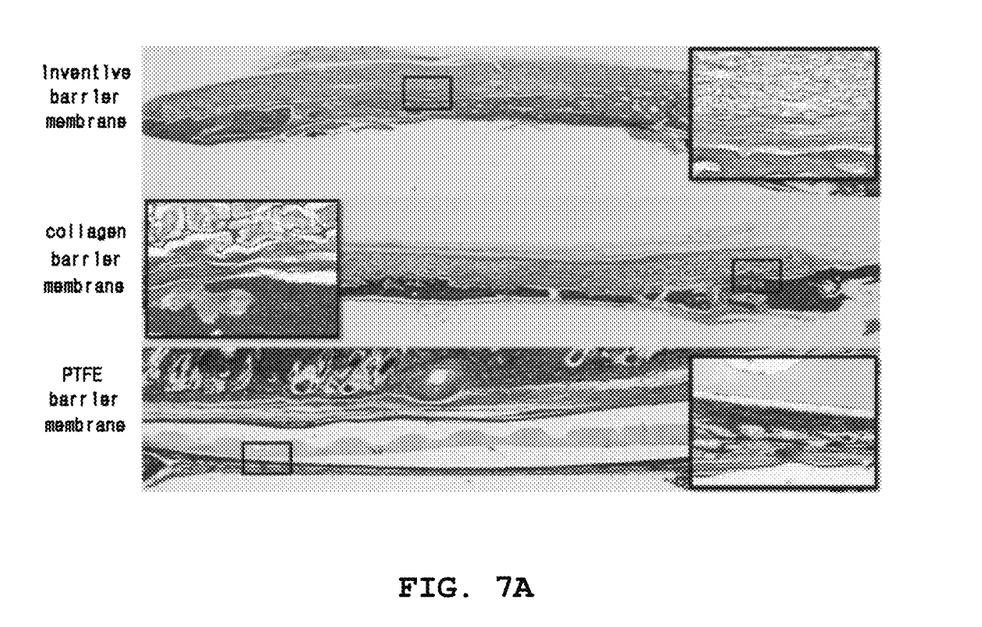
FIG. 7 shows Masson's trichrome stained images of new bone formed in bone defects at 4 weeks (a) and 8 weeks (b) after implantation with the dental barrier membrane of the present invention or control barrier membranes.

Histological images after staining with Masson's trichrome are depicted in FIG. 7. FIG. 7A shows histological images of barrier membrane-implanted bone defects at 4 weeks after implantation with barrier membranes, along with inserts of expanded views in which ossification by $Ca^{2+}$ deposition appears red.

As shown in the histological image of the bone defect implanted with the barrier membrane of the present invention, the red portion was distributed deeply across the implanted region, indicating that the barrier membrane of the present invention allowed for active osteogenesis in the bone defect.

In the expanded view for the collagen barrier membrane-implanted bone defect, part of the tissue appeared red, while almost no red portions were detected in the PTFE barrier membrane-implanted bone defect.

Figure 7B:
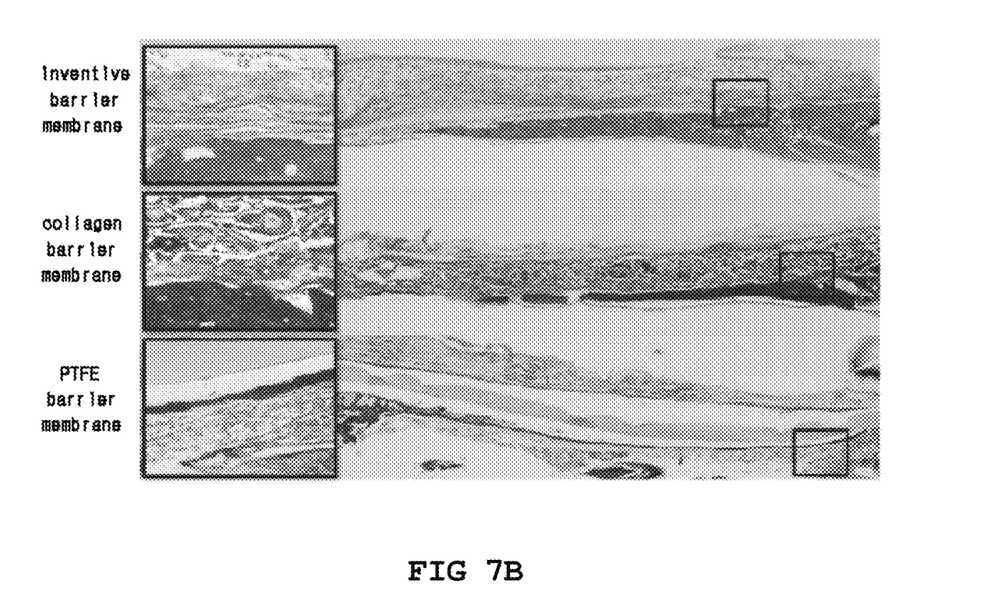

FIG. 7B shows histological images of barrier membrane-implanted bone defects at 8 weeks after implantation with barrier membranes, along with inserts of expanded views in which ossification appears blue. In the bone defect implanted with the barrier membrane of the present invention, red portions at post-operative week 4 turned blue as new bone was formed.

For the collagen barrier membrane-implanted bone defect, ossification was observed to be in progress as red colors remained around blue colors accounting for new bone. In the histological image of the PTFT barrier membrane-implanted tissue, red colors appeared, accounting for the formation of new bone. These data were consistent with the μ-CT (micro-computerized tomography) data of FIG. 6.

Figure 8:
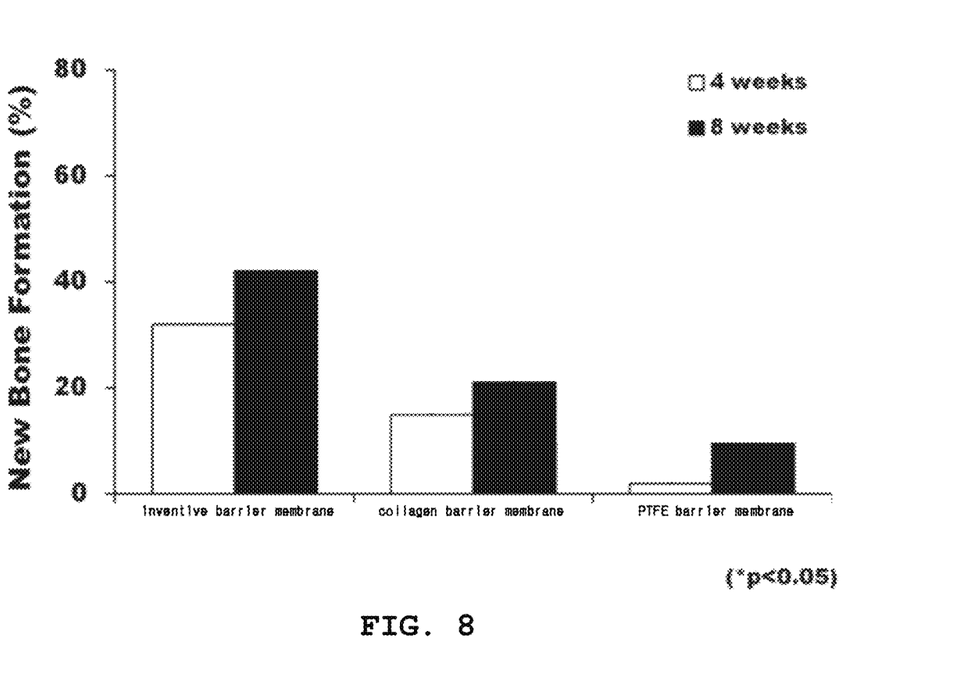
FIG. 8 is a graph showing the percentages of new bone formation in bone defects implanted with the dental barrier membrane of the present invention and with control barrier membranes.

FIG. 8 is a graph in which the percentages of new bone formation on the Y axis are plotted against barrier membranes on the Y axis, on the basis of histological analysis, with a statistical significance of $P<0.05$.

As seen, the formation rate of new bone was 30% in the bone defect implanted with the barrier membrane of the present invention at post-operative week 4, and increased to 40% at post-operative week 8. When a bone defect was implanted with the collagen barrier membrane, new bone formation was 15% at post-operative week 4 and 20% at post-operative week 8. For the PTFE barrier membrane, the formation rate of new bone was changed from 0% at post-operative week 4 to 10% at post-operative week 8. Therefore, the barrier membrane of the present invention allowed up to 4 times more new bone to be formed than did the controls.

Taken together, the data obtained above imply that the barrier membrane of the present invention exhibits an excellent bone regeneration effect on bone defects and is useful as a dental barrier membrane.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

DESCRIPTION OF NUMERICAL REFERENCES IN DRAWINGS

10: Cocoon
11: cutting line 1
13: Inside surface
15: cutting line 2
17: cutting line 3
20: Cocoon fragment with a first thickness
30: Cocoon fragment with a second thickness
31: Inner stratum
33: Mid stratum
35: Outer stratum

What is claimed is:

1. A method of manufacturing a cocoon-based dental barrier membrane for promoting osteogenesis in bone defects, comprising:
    dividing a cocoon into two or more fragments in a predetermined form, the cocoon having a shell having a first thickness; and
    implanting one of the two or more fragments onto the bone defects of a subject,
    wherein a new bone tissue is formed in the bone defects.

2. The method of claim 1, further comprising delaminating each of the fragments into a lamellar fragment having a second thickness, the second thickness being less than the first thickness.

3. The method of claim 2, further comprising packing the fragments having the second thickness prepared in the delaminating step.

4. The method of claim 1, further comprising conducting sterilization before or after each step.

5. The method of claim 2, wherein the lamellar fragment having the second thickness is an inner stratum of the cocoon.

6. The method of claim 2, wherein the lamellar fragment having the second thickness is a mid stratum of the cocoon.

7. The method of claim 2, wherein the lamellar fragment having the second thickness is an outer stratum of the cocoon.

8. The method of claim 2, further comprising conducting sterilization before or after each step.

* * * * *